(12) United States Patent
Sikiric et al.

(10) Patent No.: US 6,268,346 B1
(45) Date of Patent: Jul. 31, 2001

(54) PEPTIDES WITH ORGANO-PROTECTIVE ACTIVITY

(76) Inventors: Predrag Sikiric, Jurisiceva 5; Marijan Petek, Visnjica 29; Sven Seiwerth, Palmoticeva 17; Zelijko Grabarevic, Lermanova 12A; Ivo Rotkvic, Cvjetno naselje 1/21; Marko Duvnjak, Roza Luxemburg 4; Branko Turkovic, Bauerova 19, all of HR-41 000 Zagreb; Stiepan Mise, Ruzveltova 37, HR-58 000 Split; Ernest Suchanek, Aleja V. Popovica 125, HR-41 000 Zagreb; Boris Mildner, Kopernikova 34, HR-41 00 Zagreb; Ivan Udovicic, Ennetmoserstrasse 16, CH-6370 Stans, all of (HR)

( * ) Notice: Subject to any disclaimer, the term of this patent is extended or adjusted under 35 U.S.C. 154(b) by 0 days.

(21) Appl. No.: 09/203,921

(22) Filed: Dec. 2, 1998

Related U.S. Application Data

(63) Continuation of application No. 08/771,248, filed on Dec. 20, 1996, which is a continuation of application No. 08/185,883, filed on Aug. 23, 1994, now Pat. No. 6,211,151.
(60) Provisional application No. PCT/EP93/01352, filed on May 28, 1993.

(30) Foreign Application Priority Data

May 30, 1992 (EP) .................................................. 92109145

(51) Int. Cl.⁷ .............................. A61K 38/00; C07K 5/00; C07K 7/00
(52) U.S. Cl. .............................. 514/14; 514/15; 530/326; 530/327; 530/328
(58) Field of Search ................................... 530/326, 327, 530/328; 514/14, 15

(56) References Cited

FOREIGN PATENT DOCUMENTS 0 432 400 A2  9/1990  (EP) .............................. C07K/3/28
0 572 688 A1  5/1992  (EP) .............................. C07K/7/06

OTHER PUBLICATIONS

Hypothesis: Stomach Stress Response Diagnostic and Therapeutical Value–a New Approach in Organoprotection—Exp Clin Gastroenterol vol. 1, No. 1, pp. 15–16, 1991—Sikiric, et al.
Antiulcerogenic and Anti–Inflammatory Effect of a New Gastric Juice Peptide–body Protection Compound—Exp Clin Gastroenterol vol. 1, No. 1, pp. 17–20 1991—Sikiric, et al.
BPC in Liver Lesions, Exp Clin Gastroenterol vol. 1, No. 1, 1991—Exp Clin Gastroenterol vol. 1, No. 1, pp. 20–21, Sikiric, et al.
BPC Reduced Alloxan–Induced Diabetes Mellitus in Rats, Exp Clin Gastroenterol vol. 1, No. 1, p. 22; 1991—Sikiric, et al.
The Effects of BPC on the Delayed Type Hypersensitivity to 2,4–Dinitrophluorbenzene Demonstrated on Ear and Colon in Mice of NMRI Strain—Exp Clin Gastroenterol vol. 1, No. 1, p. 23; 1991—Sikiric, et al.
Beneficial Effect of a New Gastric Juice Peptide, Body Protection Compound, in Acute Pancreatitis Models, Exp Clin Gastroenterol vol. 1, No. 1, p. 24–25; 1991—Sikiric, et al.
Influence of BPC on Experimental Kidney Lesions Models—Exp Clin Gastroenterol vol. 1, No. 1, p. 25; 1991—Sikiric, et al.
Gastric Mucosal Preventing Effect of Body Protection Compound (BPC) on the Development of Ethanol—and HCl–Induced Gastric Mucosal Injury, Exp Clin Gastroenterol vol. 1, No. 1, pp. 87–90, 1991—Moszic, et al.
Pentadecapeptide BPC 157 Mucosal Protection and Antiinflamatory Effect, Abstract, Supp Gastroenterol, vol. 104–No. 4, Part 2, 1995—Sikiric et al.

*Primary Examiner*—Avis M. Davenport
(74) *Attorney, Agent, or Firm*—Darby & Darby

(57) ABSTRACT

Peptides having 8 to 15 amine acid residues and a molecular weight between 900 and 1600 Daltons. The peptides have a biological activity comparable to the protein BPC.

38 Claims, 7 Drawing Sheets

Deprotected peptide with Seq. Id. No: 6

```
                              SEQUENCE LISTING

<160> NUMBER OF SEQ ID NOS: 13

<210> SEQ ID NO: 1
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Leu Glu Pro Pro Pro Gly Lys Pro Ala Asp Asp Ala Leu Gly Val
  1               5                  10                  15

<210> SEQ ID NO: 2
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Gly Glu Pro Pro Pro Gly Lys Pro Ala Asp Asp Ala Gly Leu Val
  1               5                  10                  15

<210> SEQ ID NO: 3
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Leu Glu Pro Pro Pro Leu Lys Pro Ala Asp Asp Ala Leu Gly Val
  1               5                  10                  15

<210> SEQ ID NO: 4
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Leu Glu Pro Pro Pro Leu Lys Pro Ala Asp Ala Leu Gly Val
  1               5                  10

<210> SEQ ID NO: 5
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Gly Glu Pro Pro Pro Gly Lys Pro Ala Asp Ala Gly Leu Val
  1               5                  10
```

```
<210> SEQ ID NO: 6
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Glu Pro Pro Pro Leu Lys Pro Ala
 1               5

<210> SEQ ID NO: 7
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Asp Pro Pro Pro Ile Arg Pro Ala Asp
 1               5

<210> SEQ ID NO: 8
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Glu Pro Pro Pro Leu Lys Pro Ala Asp
 1               5

<210> SEQ ID NO: 9
<211> LENGTH: 14
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(14)
<223> OTHER INFORMATION: cyclic peptide

<400> SEQUENCE: 9

Leu Glu Pro Pro Pro Leu Lys Pro Ala Asp Ala Leu Gly Val
 1               5                  10

<210> SEQ ID NO: 10
<211> LENGTH: 10
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(10)
<223> OTHER INFORMATION: cyclic peptide

<400> SEQUENCE: 10

Gly Glu Pro Pro Pro Gly Arg Pro Ala Asp
 1               5                  10
```

```
<210> SEQ ID NO: 11
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Glu Pro Pro Pro Leu Lys Pro Ala Asn
 1               5

<210> SEQ ID NO: 12
<211> LENGTH: 15
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: UNSURE
<222> LOCATION: (1)
<223> OTHER INFORMATION: aliphatic amino acid  residue
<220> FEATURE:
<221> NAME/KEY: UNSURE
<222> LOCATION: (2)
<223> OTHER INFORMATION: acidic amino acid residue
<220> FEATURE:
<221> NAME/KEY: UNSURE
<222> LOCATION: (6)
<223> OTHER INFORMATION: neutral aliphatic amino acid residue
<220> FEATURE:
<221> NAME/KEY: UNSURE
<222> LOCATION: (7)
<223> OTHER INFORMATION: basic amino acid residue
<220> FEATURE:
<221> NAME/KEY: UNSURE
<222> LOCATION: (11)
<223> OTHER INFORMATION: neutral aliphatic amino acid residue
<220> FEATURE:
<221> NAME/KEY: UNSURE
<222> LOCATION: (13)..(15)
<223> OTHER INFORMATION: neutral aliphatic amino acid residue

<400> SEQUENCE: 12

Xaa Xaa Pro Pro Pro Xaa Xaa Pro Ala Asp Xaa Ala Xaa Xaa Xaa
 1               5                  10                  15

<210> SEQ ID NO: 13
<211> LENGTH: 8
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: UNSURE
<222> LOCATION: (1)
<223> OTHER INFORMATION: acidic amino acid residue
<220> FEATURE:
<221> NAME/KEY: UNSURE
<222> LOCATION: (5)
<223> OTHER INFORMATION: aliphatic amino acid residue
<220> FEATURE:
<221> NAME/KEY: UNSURE
<222> LOCATION: (6)
<223> OTHER INFORMATION: basic amino acid residue

<400> SEQUENCE: 13

Xaa Pro Pro Pro Xaa Xaa Pro Ala
 1               5
```

PEPTIDES WITH ORGANO-PROTECTIVE ACTIVITY

This is a continuation of application Ser. No. 08/771,248, filed Dec. 20, 1996, which is a continuation of Ser. No. 08/185,883 filed Aug. 23, 1994, which is a 371 of PCT/EP93/01352, filed May 28, 1993. Each of these prior applications is hereby incorporated herein by reference, in its entirety.

This invention relates to new peptides having high biological activity of the same type as the known natural compound BPC, but with shorter amino acid chains.

BACKGROUND OF THE INVENTION

A biologically active protein with organo-protective activity which was isolated from human or animal matter and named BPC (Body Protecting Compound) was disclosed in EP 0 432 400 and also published: P. Sikiric et al, Exp.Clin. Gastroenterol., 1, 15–26, 1991. This protein has a high molecular weight of about 40 000±5000 Daltons, with an only partially determined structure. This compound has a very broad spectrum of biological activities like: ulcus protective, hepatoprotective, antiviral, antiedematous, general antiinflammation activity, antimalignant activity and others. It should be used in the therapy of cited diseases, further in the therapy of diseases and disorders of nervous system, disorders of dopaminergic etiology, surgery, stomatology, in the curing of infertility and in veterinary medicine. But this broad spectrum of activity can be probably a consequence of undetermined structure or even of insufficient purity or homogeneity of the isolated compound BPC.

SUMMARY OF THE INVENTION

We have discovered synthetic peptides with only 8 to 15 amino acid residues with a molecular weight between 900 and 1600 Daltons, that have the biological activity of the natural body protecting compound BPC, but with increased selectivity. Our new peptides are more economically produced and are less subject to the effect of side reactions because they contain less amino acid residues than BPC.

BRIEF DESCRIPTION OF THE DRAWINGS

FIG. 5 illustrates the synthesis of the linear peptide with SEQ ID NO:4 and the cyclic peptide with Seq. Id. No: 9 from the partially protected linear peptide SEQ ID NO:4a.

DESCRIPTION OF THE INVENTION

Figure 1:
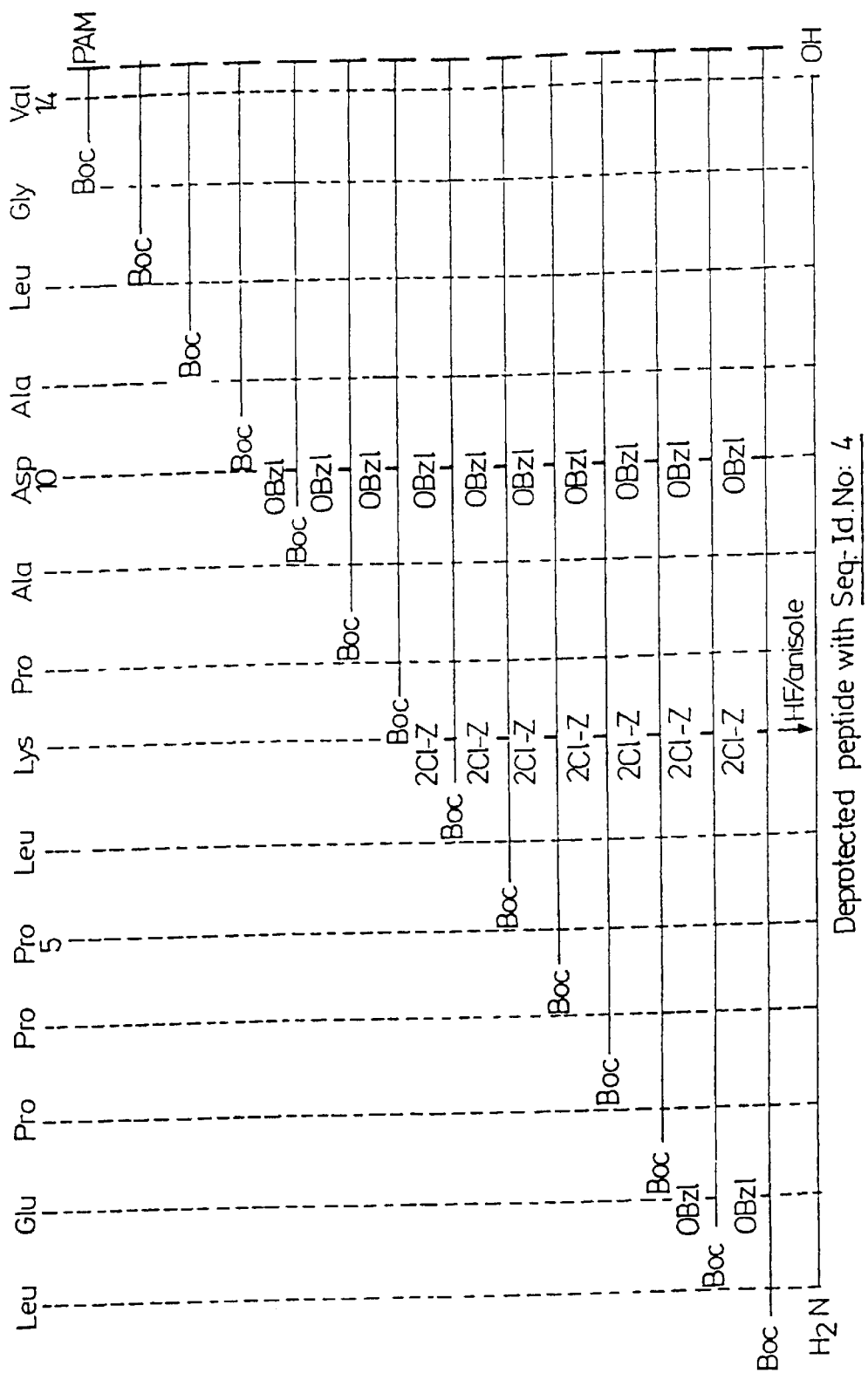
FIG. 1 illustrates the synthesis of the peptide with SEQ ID NO:4 using Boc strategy.

In accordance with one aspect of the present invention, there is provided a class of synthetic peptides which exhibit surprisingly high biological activity, especially in the sense of body protection. In any case these synthetical compounds with a well defined structure have a great advantage in comparison to the only partially defined high molecular protein BPC, which is obtainable only by a difficult procedure from dubious natural sources.

More particularly, this invention relates to a novel class of biologically highly active peptides, comprising from 8 to 15 amino acid residues, which are represented by the following structural formula using the three letter amino acid code. The numbers below each amino acid residue refer to the position of the residue in the peptide chain:

```
Xaa Zaa Pro Pro Pro Xaa Yaa Pro Ala Asp Zaa Ala Xaa Xaa Xaa
 1            5                   10                  15
``` wherein one or more amino acid residues are substituted. The substituents Xaa, Yaa and Zaa which may be employed are in the following table I.

TABLE I

| Residue | Substituent |
|---------|-------------|
| Xaa | a neutral aliphatic amino acid: Ala, bAla, Leu, Ile, Gly, Val, Nle, Nva |
| Yaa | basic amino acid: Lys, Arg, Orn. His |
| Zaa | acidic amino acid: Glu, Asp, Aad, Apm |

Preferred peptides are as follows:

```
Leu Glu Pro Pro Pro Gly Lys Pro Ala Asp Asp Ala Leu Gly Val  Seq. Id. No: 1
 1            5                   10                  15

Gly Glu Pro Pro Pro Gly Lys Pro Ala Asp Asp Ala Gly Leu Val  Seq. Id. No: 2
 1            5                   10                  15

Leu Glu Pro Pro Pro Leu Lys Pro Ala Asp Asp Ala Leu Gly Val  Seq. Id. No: 3
 1            5                   10                  15
```

In accordance with another respect of the present invention there are provided analogous peptides in amide or carboxy terminated form at C terminus, having the structural formulas hereinabove described, and wherein at least one and at most 7 amino acid residues in region 1–15 are omitted and at least one of the remaining amino acid residues can be substitued according to the described schema of substitution in table I.

Preferred peptides are as follows:

```
Leu Glu Pro Pro Pro Leu Lys Pro Ala Asp Ala Leu Gly Val    Seq. Id. No: 4
 1               5                  10              14

Gly Glu Pro Pro Pro Gly Lys Pro Ala Asp Ala Gly Leu Val    Seq. Id. No: 5
 1               5                  10              14

Glu Pro Pro Pro Leu Lys Pro Ala                            Seq. Id. No: 6
 1           5           8

Asp Pro Pro Pro Ile Arg Pro Ala Asp                        Seq. Id. No: 7
 1           5               9

Glu Pro Pro Pro Leu Lys Pro Ala Asp                        Seq. Id. No: 8
 1           5               9
```

In accordance with another embodiment, peptides having the structural formulae hereinabove described, and wherein at least one of amino acid residues can be omitted and at least one of the remaining amino acid residues can be substituted as indicated in table I, are transformed in cyclic form by the formation of a new bond CO—NH between the first and the last amino acid residues in the molecule. Preferred peptides are as follows:

```
                                                           Seq. Id. No: 9
Leu Glu Pro Pro Pro Leu Lys Pro Ala Asp Ala Leu Gly Val
 |   2           5                  10              13 |

Seq. Id. No: 10
Gly Glu Pro Pro Pro Gly Arg Pro Ala Asp
 |   2           5               9 |
```

Applicants have found that when employing the peptides as hereinabove described, such peptides display biological activity equal to or greater than the parent protein BPC.

Pharmacological investigation of the described peptides has been done on different common models "in vitro" and "in vivo" and the following pharmacological properties were found:

1.) Gastric ulcer induced by restraint stress

Albino Wistar (male) rats (180–200 g), were used in the experiments. All the animals were immobilized in a supine position for 48 hours at room temperature. Immediately thereafter they were sacrificed and the lesions measured. The peptides Seq. Id. No: 4, 6 and 2 were applied in a dosage of 10 μg or 10ng/kg b.w., i.p. or i.g. 1 hour before noxious procedure.

Both i.g. and i.p. applications, even in such low doses as 10 ng/kg b.w. were strongly protective.

2. Cysteamine model of ulcer

Albino Wistar (female) rats (180–200g), were used in the experiments. Cysteamine hydrochloride (dissolved in distil. water) in a dose of 400 mg/kg b.w., s.c. was applied. 24 hours later the animals were sacrificed. The peptides Seq. Id. No: 4 was applied in a dosage of 1.0 μg, 100 ng and 50 ng/kg b.w., i.p. and i.g. A strong and dose dependent protection was obtained. The same activity was found for both i.p. and also for intragastrical routes of administration.

3. Turpentine induced buccal edemas

Animals: Wistar male rats (180–240g), N=10 in each group. Turpentine was given intramucosally 0.02 ml/rat. Control: 0.9% saline intramucosally (0.02 ml/rat, 2 x). Peptides Seq. Id. No: 2 and 4 were applied in a dosage 10 μg and 10 ng/kg, i.p. and i.g., 1 hour before turpentine. Buccal edemas were measured 24 hours after edema induction. Statistical analysis: Mann-Whitney test. The investigated peptides were effective in a dosage of 10 μg/kg b.w.

4. Surgery: the effect on skin incissions

Male Albino rats (10 for each experiment, 200–250g b.w.) were used in the experiments. The rats with skin wounds were individually maintained in separate cages. On each animal under light aether anaesthesia after the back skin showing 3 cm incissions were placed in parallel through the skin 1.5 cm of either site of the midline. One wound was then coapted with two surgical clips, and the other left untreated. Peptide Sea. Id. No: 4, dissolved in saline, in doses of 1.0 μg and 1.0 ng/kg b.w., or saline 0.5 ml/kg b.w. in control, was applied intradermally between the wounds immediately after the injury.

A prominent healing effect of the investigated peptide was obvious on both wounds with surgical clips as well as those left without surgical treatment. After 5 days the treated group showed a smaller number of inflammatory cells and significantly better developed reticulin fibres than in the control.

5. Effect on experimental burns

Male albino rats, Wistar strain (N=10, 200–250 g b.w.) were used in the experiment. Under light aether anaestesia the nasal mucosa was exposed to a glowing cauter during 5 seconds. The peptide Seq. Id. No: 4 was used in a dosage of 10μg/kg b.w., i.p. 1 hour before injury induction. Control: 5.0 ml/kg b.w. of saline, i.p. The applied procedure usually produced a prominent swelling of the snout and was regularly fatal for controls (but not for treated animals!) within nine postwounding days. In contrast to controls, only very modest posttraumatic swelling of the snout was observed. Subsequently the normal nasal respiration was only slightly impaired and survival undisturbed.

6.) Effect on fracture healing

Male Albino rats of Wistar strain (270–300 g b.w.) were used in the experiments. Left tibias were fractured manually in the middle part of the bone under aether anaesthesia. No immobilization was used and animals were allowed to move freely in cages. The animals were sacrificed on the $5^{th}$, $8^{th}$, $12^{th}$ and $30^{th}$ day after the injury induction.

Peptide Seq. Id. No: 4 was given in a dosage of 10.0 μg/kg b.w., i.p., 1 hour before injury and subsequently once daily (last application 24 h before sacrifice). Control group received simultaneously an equivuolume of saline (0.9%, 5.0 ml/kg b.w., i.p.). A significantly improved healing rate was noted in all peptide treated animals at each of the investigated intervals. All treated animals showed consistently lower local posttraumatic hematome than control animals and they restored their lesioned function quite sooner.

7.) Antiviral activity

Antiviral activity was investigated on new-born mice, BALB-C strain, 24 hours old, both sexes.

ARBO-viruses: TBE (=Tick Borne Encephalitis), Bhania, Dengue 1,2,3,4, Sinbis, West-Nile, Calovo, Hepatitis A, LCM (*Limphatic choriomeningitis*) and Herpes type I were applied as a virus suspension in dilution $10^{-2}$ (0.02 ml/mouse), prepared as is generally accepted, and injected i.c. or p.o. (Hepatitis A). In view of the difference in virulence the doses were adjusted in such a way as to be comparable regarding $LD_{100}$ in 0.02 ml i.c. (or p.o., Hepatitis A) inoculum in a $10^{-2}$ dilution. In this way, we were able to compare the course of different virus infections, regardless of possible inoculation of different virus concentrations.

The peptide Seq.Id.No: 4 was used in a concentration of 20.0 μg/ml in a 0.9% saline solution and applied only once in a dosage of 2.0 μg/kg b.w., i.c. or i.p.:

a) 2 hours before virus application ($-2^h$)
b) simultaneously with infection (0).

Control: the same volume of the saline i.c. or i.p. The results are summarized in Table II.:

The numbers in the table indicate the period (days) until all virus infected mice in peptide or saline (control) treated groups succumbed.

| | TREATMENT | | | | | | | |
|---|---|---|---|---|---|---|---|---|
| | Saline | | | | synthetic fragment 4 | | | |
| Viruses | $-2h^x$ | | $0^x$ | | $-2h^x$ | | $0^x$ | |
| infections | i.p. | i.c. | i.p. | i.c. | i.p. | i.c. | i.p. | i.c. |
| TBE[a] | 5 | 5 | 5 | 5 | n.d. | n.d. | 20 | 20 |
| Bhania[a] | 5 | 5 | 5 | 5 | n.d. | n.d. | 20 | 20 |
| Dengue 1[a] | 5 | 5 | 5 | 5 | n.d. | n.d. | 20 | 20 |
| Dengue 2[a] | 5 | 5 | 5 | 5 | n.d. | n.d. | 20 | 20 |
| Dengue 3[a] | 5 | 5 | 5 | 5 | n.d. | n.d. | 20 | 20 |
| Dengue 4[a] | 5 | 5 | 5 | 5 | n.d. | n.d. | 20 | 20 |
| Sinbis[a] | 5 | 5 | 5 | 5 | n.d. | n.d. | 20 | 20 |
| WestNile[a] | 5 | 5 | 5 | 5 | n.d. | n.d. | 20 | 20 |
| Calovo[a] | 5 | 5 | 5 | 5 | n.d. | n.d. | 15 | 15 |
| Hepatitis A[+] | 5 | 5 | 5 | 5 | n.d. | n.d. | 20 | 20 |
| LCM | 5 | 5 | 5 | 5 | n.d. | n.d. | 20 | 20 |
| Herpes type 1 | 5 | 5 | 5 | 5 | n.d. | n.d. | 20 | 20 |
| None (Healthy) | n.d. | n.d. | n.d. | n.d. | n.d. | n.d. | n.d. | n.d. | n.d. non determined: animals have been observed during 40 days after viruses application. No death has been noted.
[a]ARBO-viruses
[+]peroral viruses application
[x]the animals were treated 2h before viruses application (−2h) or simultaneously with viruses administration (0)
[o]vs. saline P < 0.001; 8 mice per each group 8.) Antidepression activity For determining antidepressant activity the forced swimming test according Porsolt et al, Eur.J.Pharmacol., 47, 379–391,1978, was used.

Male Wistar rats (180–240 g b.w.) were used for this experiment. The investigated peptide Seq.Id.No: 4 was given at the first day after pretest session and at the second day one hour before experiment (i.p.).

Control group: saline, i.p.

The animals were observed for 5 minutes. The time of immovability was measured ($T_i$).

$T_i$ in the control group was about 150 sec., and in the peptide treated group was only 60–70 sec. This effect was from long duration: after 16 days was still present.

Dose response:

10 μg to 10 ng/kg: full effect 10 pg/kg: effect still present
1 pg/kg: effect in disappearance.

9.) Effect on model of Parkinson disease

For investigation the well known models for Parkinson disease were used (Karakola s. et al, Pharmacol. Toxicol., 67, 95–100, 1990): reserpine model and MPTP model.

NMRI- Hannover male (for MPTP model) or both sexes (for reserpine model) mice were used.

a) MPTP was applied in a dosage of mg/kg b.w., i.p. once daily for six subsequent days, and then for next four days in a higher dosage of 50 mg/kg b.w. The investigated peptide Seq.Id.No: 4 was applied in a dosage of 1.5 μg and 15.0 ng/kg b.w., i.p., 15 min. before each MPTP administration or 15 min. after each MPTP administration.

b) Reserpine was applied in a dose of 5mg/kg b.w., i.p. The tested peptide was applied in a dosage of 10 μg or 10 ng/kg b.w., i.p. 15 minutes before reserpine or 24 hours following reserpine administration in the same dosage.

Controls: an equal volume of saline, 5 ml/kg b.w. i.p.

A significant reduction of hypokinesia, rigidity (catalepsy) and tremor were observed after pretreatment with peptide.

In the MPTP model the pretreatment with this peptide strongly abolished the catalepsy development and diminished the akinesia and tremor appearance.

Posttreatment (after 15 min) strongly prevented the further development of MPTP catalepsy and markedly diminished akinesia and tremor. A usually a high mortality (50%) noted after only one application of MPTP was decreased in peptide pretreated as well in posttreated animals.

10.) The effect of peptide administration in haemorrhagic shock

Adult female Albino rats of Wistar strain (150–180 g) have been used in all the experiments.

The effects on haemorrhagic shock were investigated in two series of experiments.

a) The animals were bled (1 ml over 3 minutes, 2 minutes of the rest) until death. The removed blood volume producing fatal outcome was assessed in peptide Seq.Id.No: 4 (10.0 μg or 10 ng/kg b.w., i.p.) or saline (5.0 ml/kg b.w., i.p.) pretreated (15 min. before bleeding) animals. A significantly higher fatal blood volume loss in comparison with the control values was consistently noted in the group treated with the higher dose of peptides.

b) The blood pressure was lowered by controlled blood volume removal and thereafter sustained at the 30–35 mm Hg values for a 5 minutes period.

Then, the peptide Seq.Id.No: 4 (10.0 μg or 10.0 ng/kg b.w.) or saline (control, 3.0 ml/kg b.w.) were i.v. applied. Contrasting with the controls, significantly raised and sustained blood pressure values and complete death abolition were noted in peptide treated animals.

Therefore, it seems that the investigated peptide is highly effective in ameliorating the consequences of the blood volume loss.

11.) The influence on lethal radiation NMRI - Hannover mice, 5–6 weeks old, of both sexes (18–22 g b.w.) were used in the experiments. Synthetic peptide Seq.Id.No: 4 was applied in a dosage of 20 μg/kg b.w., i.p. 1 hour before or after irradiation. The control animals received simultaneously an equivolume of 0.9% saline i.p. (5.0 ml/kg). Naive, healthy animals kept in usual conditions, not subjected to drugs or irradiation treatment served as healthy control.

Irradiation: Teatron 80 (Co 60, 2200 Ci). The unanaesthetized mice in cages, 16 mice per group, were exposed to whole body irradiation with a supralethal dose of 9 Gy in an irradiation area of 20×20 cm, distance 80 cm.

Deaths were recorded twice daily for 30 days.

All control animals died within 7–12 days ($LD_{100/12}$)

No death was noted in healthy (non irradiated) controls.

Relative to the control data, no difference was observed in groups treated with peptide 1 hour after irradiation. However, a significant survival was noted when the compound was applied 1 hour before radiation.

A 70% increase in $LD_{100}$ relative to the control could be noted.

12. Influence on induced malformation

NMRI - Hannover female mice, two months old, 25 g b.w., but not previously exposed to copulation were used in all experiments. The female mice in the estrus phase were mated overnight with well experienced healthy male mice. The mice were sacrified after 20 days of pregnancy.

Vitamin A was applied in a dose of 15700 U/kg b.w., i.m., at tenth day of the pregnancy (0.05 ml/kg b.w.). Peptide Seq.Id.No: 4 was given simultaneously in a dosage of 10 μg or 10 ng/kg b.w.,i.p.

Control: saline 5.0 ml/kg b.w., i.p.

Animals non treated with vitamin A receiving at the same time i.p. saline or peptide 4 in the same dosage served as healthy control.

No malformation was noted in the healthy (saline) or peptide treated group.

The results summarized in the Table III. show surprisingly a significant and dose dependent protective effect of investigated peptide against vitamin A induced malformations.

TABLE III

Macroscopic examination

| Treatment | Total number of fetuses | Number of malformed fetuses |
|---|---|---|
| control group (saline) | 55 | 0 |
| vitamin A | 54 | 36 |
| vitamin A + peptide 4 10 ng/kg | 36 | 13 |
| vitamin A + peptide 4 10 μg/kg | 18 | 1 |

13.) Acute toxicity

Acute toxicity of synthetic peptides was determined in female mice (weight ca. 20 g). Groups of 6 animals were used for each experiment and control.

Peptides Seq.Id.No: 2,3,4 and 6 were applied in a dosage of 8, 25 and 50 mg/kg b.w., i.v. Control group was treated with saline (0.9%, 5.0ml/kg b.w.). The animals were observed for signs of toxicity for next 15 days.

In the applied dosage no signs of toxicity or death was observed. An interesting phenomenon of significantly increased motility and livelines in duration of 2 hours after application of peptides was observed.

In view of the results of the pharmacological investigations these peptides exhibit activity to protect organisms against stress and diseases; in general to normalize organic functions.

Their use should be also effective for prevention and therapy of several human or animal diseases and disorders. More particularly, these compounds will be used for the treatment of:

stress induced disorders and diseases, gastrointestinal ulcers of diverse etiology, inflammation and edemas of diverse etiology traumas, burns, bone fractures and generally in surgery, viral infections, shock, Parkinson's disease, for protection of damages of radiation, for protection of malformations.

In general, the described peptides can also be employed in a wide variety of pharmaceutical compositions in combination with a non-toxic pharmaceutical carrier or vehicle such as a filler, a non-toxic buffer, or physiological saline solution. Such pharmaceutical compositions can be used topically or systemically and can be in any suitable form such as a liquid, solid, semi-solid, injectable solution, tablet, ointment, lotion, capsule, lingualette or the like.

These peptides will be in general administered in a dosage of from $10^{-5}$ to $10^{-2}$ mg/kg of body weight, when applied systemically. When administered topically, they will be used in a higher concentration, e.g. 0.1% to 0.5%.

Very favorable is the absence of any signs of toxicity until doses of 50 mg/kg b.w. and also good activity of compounds by peroral administration (intragastrically).

The peptides described herein can be synthesized using step by step condensation or protected amino acids in a homogenous liquid system or preferable using solid phase method. For preparation of cyclic peptides partially protected linear peptides of desired length are prepared as with an alkyl ester group on C-terminus, which is converted into azide, following coupled and deprotected. Alternatively, partially protected linear peptide with free terminal groups can be cyclized by diphenylphosphorylazide in very diluted solution.

The invention will now be described with respect to the following examples, however, the scope of the present invention is not intended to be limited thereby.

EXAMPLE 1

Peptide synthesis using Boc strategy

Peptide synthesis was performed beginning with 100 mg of Boc-Val-PAM resin to produce C-terminal carboxy peptide (PAM purchased from Applied Biosystems, substitution 0.56 meq/g is an amino-acyl-4-(oxymethyl)-phenylacetic acid derivative of aminopolystyrene). Boc amino acids (Boc=tert.-butoxycarbonyl-) were condensed one after other on polymer carrier using diisopropylcarbodiimide (DIPC) as condensation reagent. In each step Boc group was removed with 50% solution of trifluoroacetic acid (TFA) in dichloromethane. Amino group was then deprotonated with diisopropylethylamine.

The conversion in each step should be higher than 99.5%. If not, the condensation was repeated. After complete synthesis, cleavage was performed using low HF procedure (2 hours at 0° C.). As carbonium ion scavenger was used anisole. HF was evaporated by a flow of nitrogen. Crude raw peptide was then obtained by pouring of oily residue into dry ether.

Then the raw peptide was purified by reverse phase HPLC using column 5×150 mm filled with silica gel RP-18, gradient elution with solvent system: 0.1% TFA in water/acetonitrile. Detection: ultraviolet absorbtion at 225 nm.

The synthesis of the peptide with Seq.Id.No: 4 is depicted in FIG. 1.

EXAMPLE 2

Peptide synthesis using Fmoc strategy

Standard Fmoc protected amino acids were used for the synthesis (Fmoc=9-fluorenylmethyloxy-carbonyl-). The side chain functions were protected as O-tert. butyl esters (Asp, Apm, Glu, Aad) and as Boc derivatives (Lys). First amino acid (Val) was bonded on to polymeric carrier-BHA resin (BHA=benzhydrilamino resin) using diisopropyl-carbodiimide as coupling reagent. In each step the Fmoc protective group was removed with piperidine. Thereafter the second and so on all next amino acids were introduced using the same way until the synthesis is completed. The cleavage was done by a mixture of TFA/TFMSA/anisole= 2:17:52 (vol/vol).

Peptide was then purified using the HPLC method described in example 1.

Figure 2:
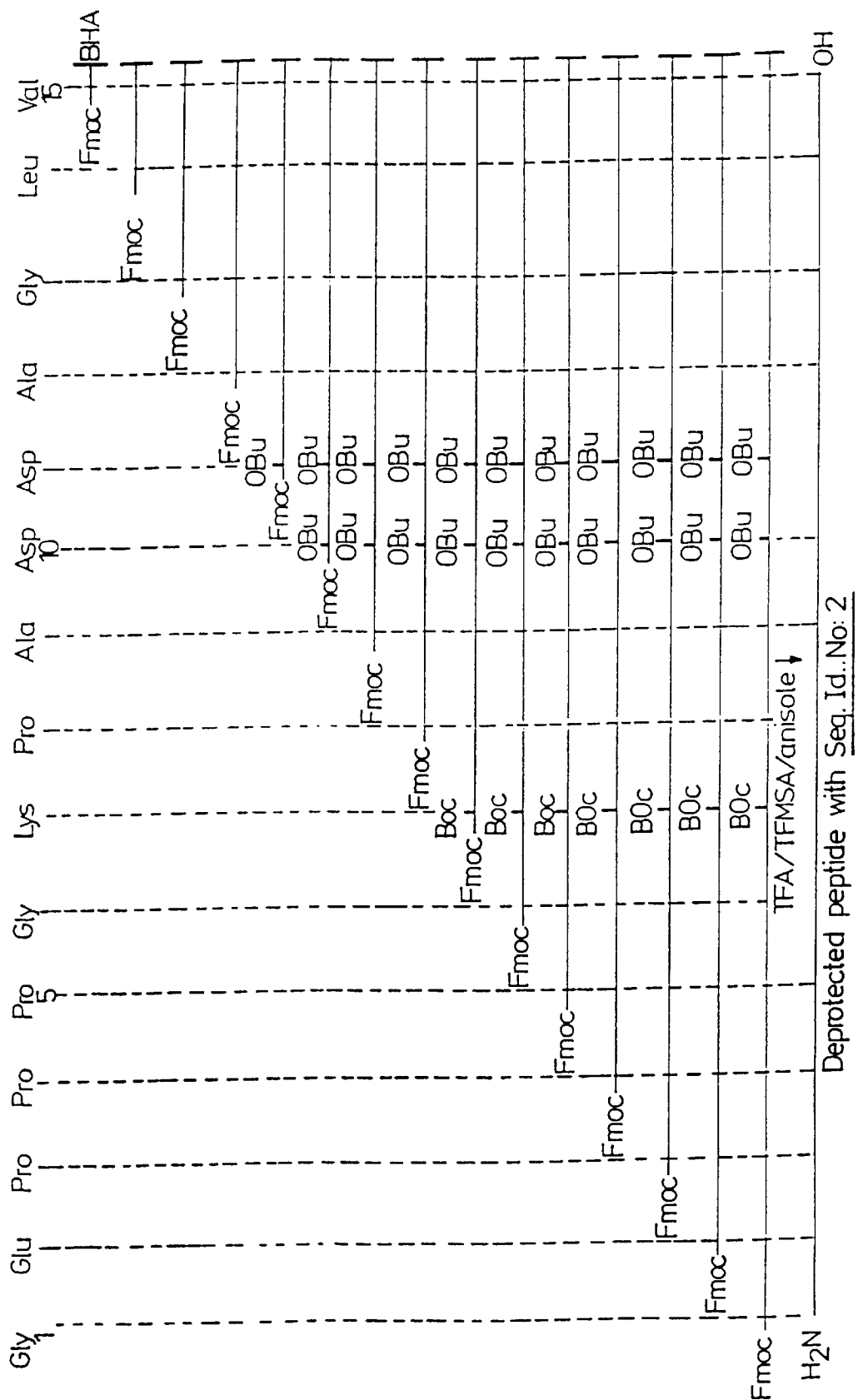
FIG. 2 illustrates the synthesis of the peptide with SEQ ID NO:6 using Fmoc strategy.

The synthesis of the peptide with Seq.Id.No: 2 is illustrated in FIG. 2.

EXAMPLE 3

Peptide synthesis using Ddz strategy

All amino acids were used protected at their α-amino function by Ddz (=α, α-dimethyl-3,5-dimethoxybenzyloxycarbonyl-). The side functions were protected by Z group (=benzyloxycarbonyl-) for lysine and O-t-Bu group (t-butylester) for aspartic and glutamic acid.

A Merrifield support (crosslinked chloromethylated polystyrene gel) with capacity of 1.4 mmol/g was used for bonding of the first Ddz-amino acid via its cesium salt. After condensation with dicyclohexylcarbodiimide (DCC) was removed the Ddz protection group in each step with 5% TFA in dichloromethane, following by washing and deprotonation with 10% triethylamine in dichloromethane. After deprotonation the next coupling step was mediated, using the same method. These coupling steps were repeated until peptide sequence was completed.

Figure 3:
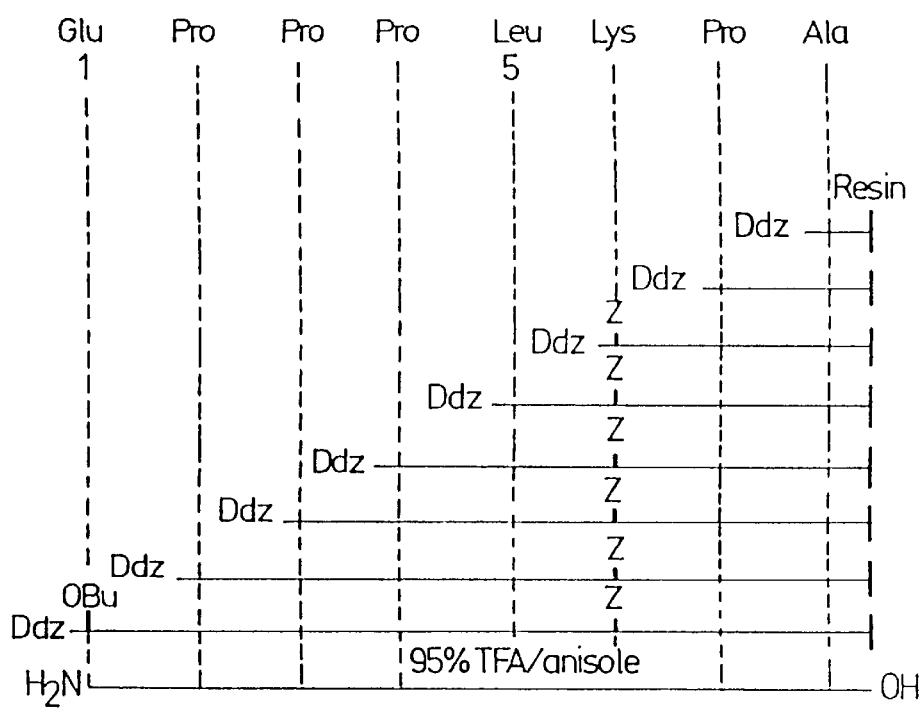
FIG. 3 illustrates the synthesis of the peptide with SEQ ID NO:6 using Ddz strategy.
Figure 6A:
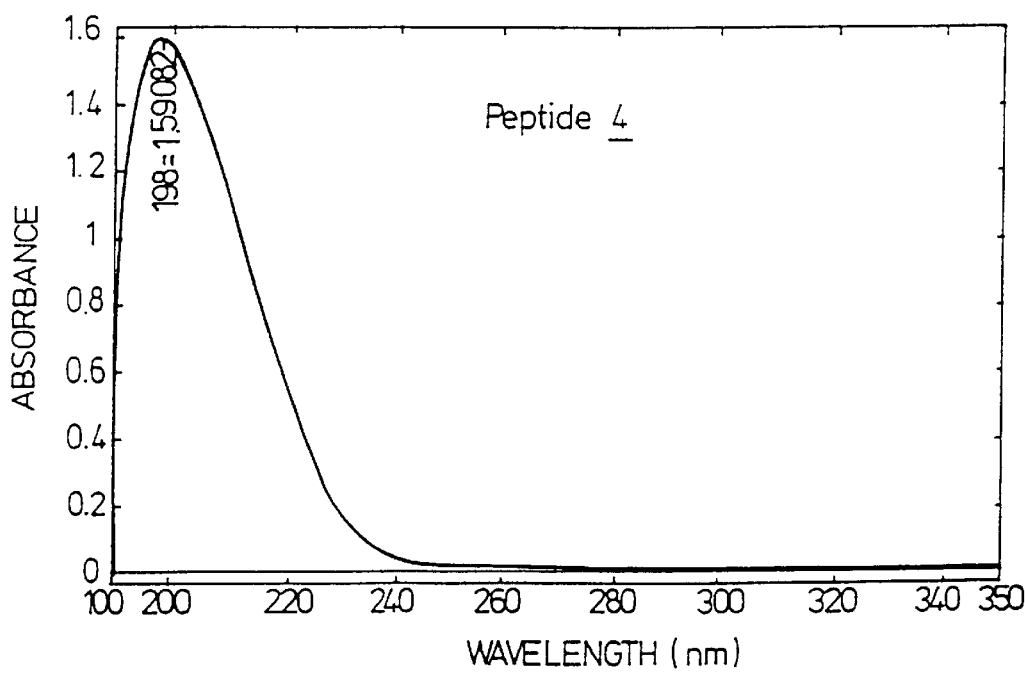
FIGS. 6(a) and 6(b) show the ultraviolet spectra of peptides with SEQ ID NO:4 and SEQ ID NO:6, respectively.

Finally the peptide was cleaved from polymeric carrier using a mixture HBr/TFA/anisole. After evaporation of volatile part the just cleaved peptide was precipitated from dry ether and dried. The raw peptide was then purified by HPLC method as described in example 1. The synthesis of the peptide with Seq.Id.No.: 6 is illustrated in FIG. 3.

EXAMPLE 4

Synthesis of cyclic peptide

Peptide in partially protected form:

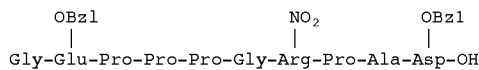

was previously prepared according to the method described in Example 1 or 2.

The 0.0005 molar solution of this peptide in dimethylformamide was cyclized after addition of diphenylphosphorylazide and triethylamine at 20° C. for 12 hours.

Then this mixture was hydrogenated with hydrogen/palladium charcoal catalyst at 25° C. for 8 hours.

The solvent was carefully evaporated and crude product purified using HPLC method described in Example 1.

Cyclic peptide with Seq.Id.No: 10

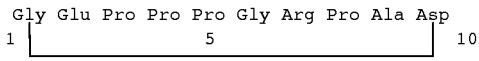

was obtained in 10% yield.

EXAMPLE 5

Synthesis of linear and cyclic peptides using the Ddz strategy

The same strategy with the Ddz protecting groups was used for obtaining of linear and cyclic peptides. The side functions were protected with Z group (lysine) and with O-benzyl ester groups—OBzl—(glutamic and aspartic acid).

Polymeric carrier was HYCRAM® resin (trademark of ORPEGEN, Heidelberg, Germany), which is 4-bromacrotonyl-β-alanyl-amidomethyl-polystyrene. The first amino acid (Ddz-valine) was bonded onto polymer carrier via its cesium salt.

Then the Ddz group was removed using trifluoroacetic acid (5%) in dichloromethane and amino group deprotonated with diisopropylethylamine.

In the next step Ddz-glycine was coupled onto valine residue in polymer matrix using diisopropylcarbodiimide (DIPC) in the presence of 1-hydroxybenzotriazole.

These steps were repeated until peptide chain was completed. The synthesized peptide in protected form was then cleaved carefully from HYCRAM® carrier with tetrakis-(triphenyl-phosphino)-palladium (O) dissolved in anhydrous tetrahydro-furan in absence of oxygen. An additive like morpholine was used as acceptor molecule for allylic groups.

Polymeric carrier was filtered off and washed with tetrahydrofuran. The solution of peptide was then filtered through a short column of silica gel to remove the palladium catalyst.

The eluate which contains the partially protected peptide 4a. was dried after evaporation of solvent in vacuum.

Synthesis of linear peptide with Seq.Id.No: 4

Partially protected peptide 4a. was dissolved in 2,2,2-trifluoroethanol and hydrogenated in the presence of palladium on charcoal (10%) with hydrogen gas at 30° C. The catalyst was filtered off and solvent evaporated in vacuum. The crude residue was then purified using HPLC method as described in Example 1. After purification the peptide with Seq.Id.No: 4 was obtained. The product was identical with compound obtained in Example 1.

Synthesis of cyclic peptide with Seq.Id.No: 9

Partially protected peptide 4a was dissolved in dimethylformamide/dichloromethane (1:1) to form 0.001 molar solution. For cyclisation DIPC and HOBt were added and left to stand at 20° C. for 10 hours. Then the solution was concentrated to small volume, diluted with 2,2,2-trifluoroethanol and purified by passing of column filled with Sephadex LH-20. Fractions containing the partially protected cyclic peptide 9a were collected and hydrogenated with palladium on charcoal (10%) catalyst at 30° C. by hydrogen bubbling and intensive shaking for 8 hours.

Then the catalyst was removed by filtration and solution dried by solvent evaporation in vacuum. The crude raw peptide was additionally purified by HPLC using the described method from Example 1. The obtained pure cyclic peptide was identified as peptide with Seq.Id.No: 9.

Figure 4:
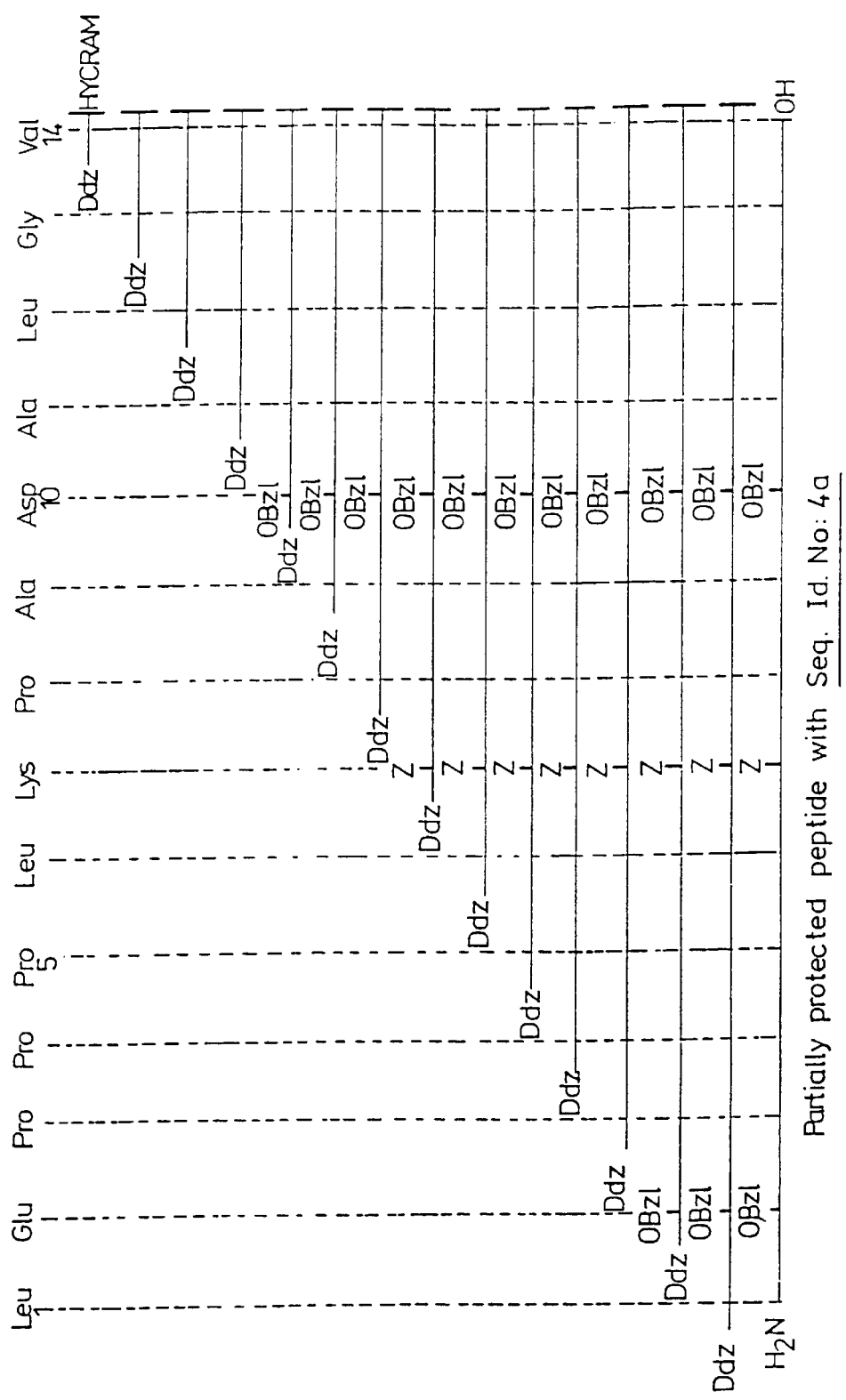
FIG. 4 illustrates the synthesis of partially protected peptide with SEQ ID NO:4a using Ddz strategy.
Figure 5:
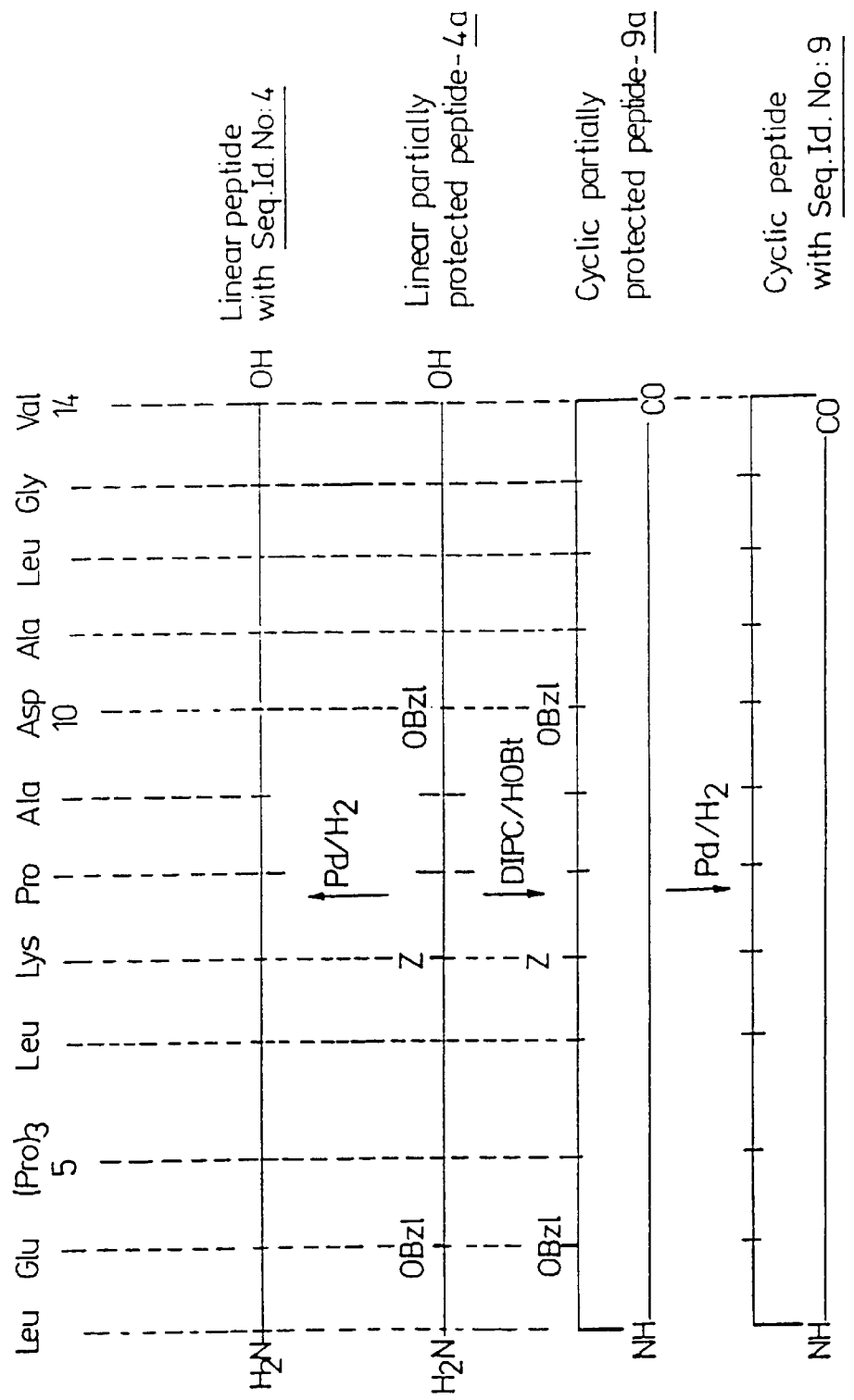
Figure 6B:
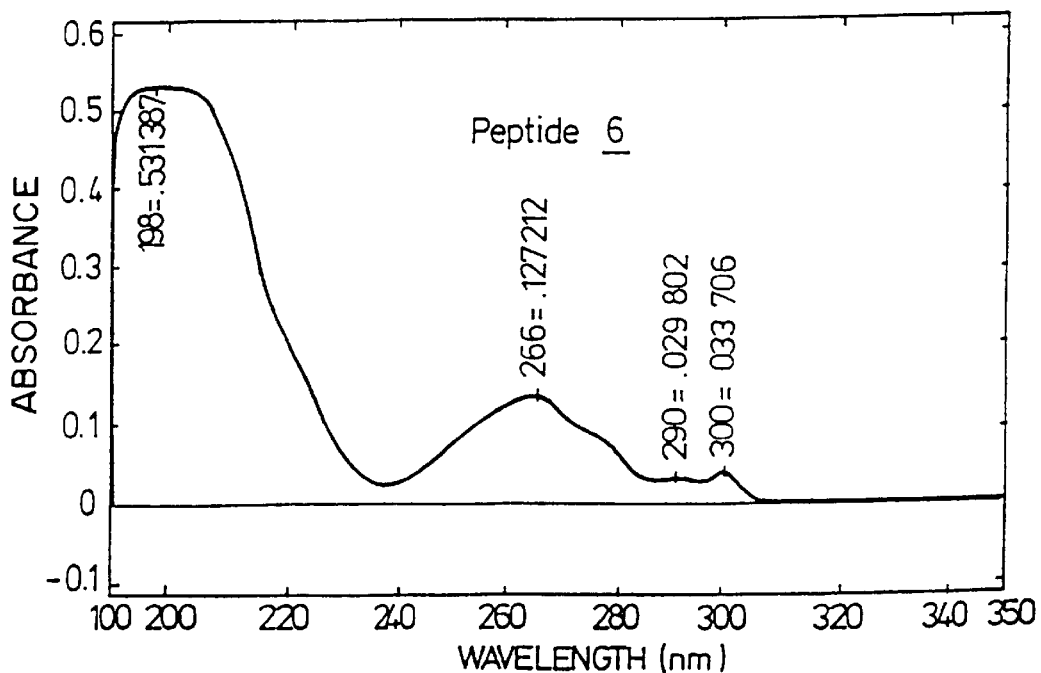
Figure 7A:
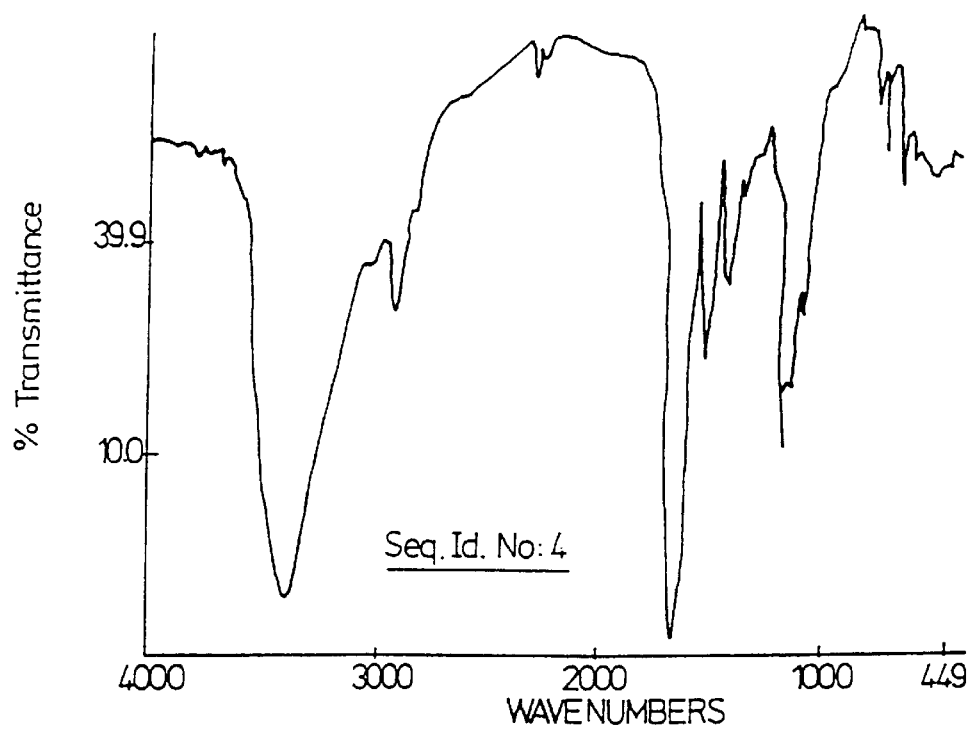
FIGS. 7(a) and 7(b) show the infrared spectra of peptides with SEQ ID NO:4 and SEQ ID NO:6, respectively.
Figure 7B:
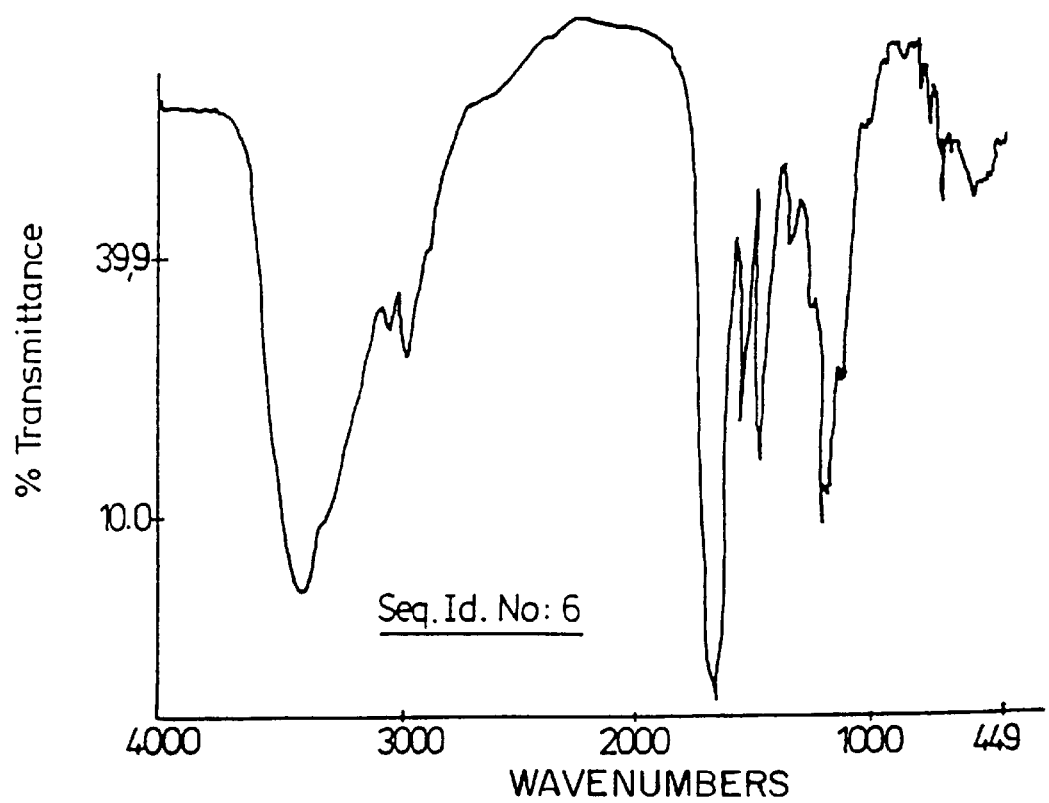

The synthesis on HYCRAM® polymer carrier using Ddz strategy and cyclisation are illustrated in FIGS. 4 and 5. All synthesized peptides were checked on their purity by HPLC method using column with silica gel RP-18 (octadecyl-silanized), eluted with a mixture of solvents consisting of water/acetonitrile/trifluoroacetic aced gradiently in usual mode. In all cases the purity was higher than 95%.

Peptides were characterized with amino acid analysis (values were within=10% of theory), sequence analysis, molecular weight determined by mass—FAB spectrometry, ultraviolet and infrared spectra (FIGS. 6(a) and 6(b) and FIGS. 7(a) and 7(b), respectively).

While only certain embodiments of the invention have been described in specific detail it will be apparent to those skilled in this art that many other specific embodiments may be practiced and many changes may be made, all within the spirit of the invention and the scope of the appended claims.

What is claimed is:

1. A biologically active peptide consisting of from 8 to 14 amino acid residues and represented by the formula:

```
Xaa Zaa Pro Pro Pro Xaa Yaa Pro Ala Asp Zaa Ala Xaa
1           5                   10
Xaa Xaa
    15
``` in which:

Xaa signifies a neutral aliphatic amino acid residue selected from the group consisting of Ala, bAla, Leu, Ile, Gly, Val, Nle and Nva, Yaa signifies a basic amino acid residue selected from the group consisting of Lys, Arg, Orn, and His, and Zaa signifies an acidic amino acid residue selected from the group consisting of Glu, Asp, Aad, and Apm;

and wherein at least one and at most seven amino acid residues in region 1 to 15 are omitted.

2. A biologically active peptide having a molecular weight of 900 to 1600 Daltons and including the sequence:

```
    Zaa Pro Pro Pro Xaa Yaa Pro Ala
    1           5           8
``` wherein

Xaa signifies a neutral aliphatic amino acid residue selected from the group consisting of Ala, bAla, Leu, Ile, Gly, Val, Nle, and Nva, Yaa signifies a basic amino acid residue selected from the group consisting of Lys, Arg, Orn, and His, and Zaa signifies an acidic amino acid residue selected from the group consisting of Glu, Asp, Aad, and Apm.

3. Peptide according to claim 1, with Seq. Id. No:7 of the formula:

```
    Asp Pro Pro Pro Ile Arg Pro Ala Asp.
    1           5               9
```

4. Peptide according to claim 1, with Seq. Id. No: 8 of the formula;

```
    Glu Pro Pro Pro Leu Lys Pro Ala Asp.
    1           5               9
```

5. Peptide according to claim 2, with Seq. Id. No:6 of the formula:

```
    Glu Pro Pro Pro Leu Lys Pro Ala.
    1           5           8
```

6. Peptide according to claim 2, with Seq. Id. No:7 of the formula:

```
    Asp Pro Pro Pro Ile Arg Pro Ala Asp.
    1           5               9
```

7. Peptide according to claim 2, with Seq. Id. No:8 of the formula:

```
    Glu Pro Pro Pro Leu Lys Pro Ala Asp.
    1           5               9
```

8. Peptide according to claim 2, with Seq. Id. No: 10 of the formula:

```
    Gly Glu Pro Pro Pro Gly Arg Pro Ala Asp.
    |  2           5               9      |
```

9. Peptide according to claim 2, with Seq. Id. No: 11 of the formula:

```
    Glu Pro Pro Pro Leu Lys Pro Ala Asn.
    1           5               9
```

10. A composition comprising the peptide of claim 2.

11. A peptide according to the claim 1 wherein the molecule is cyclized by an amide bond between first and last amino acid residue.

12. Peptide according to claim 2 with Seq.Id.No: 1 of the formula:

```
Leu Glu Pro Pro Pro Gly Lys Pro Ala Asp Asp Ala Leu Gly Val .
1               5                   10                  15
```

13. Peptide according to claim 2 with Seq.Id.No: 2 of the formula:

```
Glu Glu Pro Pro Pro Gly Lys Pro Ala Asp Asp Ala Gly Leu Val.
1               5                   10                  15
```

14. Peptide according to claim 2 with Seq.Id.No: 3 of the formula:

```
Leu Glu Pro Pro Pro Leu Lys Pro Ala Asp Asp Ala Leu Gly Val.
1               5                   10                  15
```

15. Peptide according to claim 1 with Seq.Id.No: 4 of the formula:

```
Leu Glu Pro Pro Pro Leu Lys Pro Ala Asp Ala Leu Gly Val.
1               5                   10              14
```

16. Peptide according to claim 1 with Seq.Id.No: 5 of the formula:

```
Gly Glu Pro Pro Pro Gly Lys Pro Ala Asp Ala Gly Leu Val.
1               5                   10              14
```

17. Peptide according to claim 1 with Seq.Id.No: 6 of the formula:

```
        Glu Pro Pro Pro Leu Lys Pro Ala.
        1               5           8
```

18. Peptide according to claim 1 with Seq.Id.No: 9 of the formula:

```
Leu Glu Pro Pro Pro Leu Lys Pro Ala Asp Ala Leu Gly Val.
    2               5                   10          13
```

19. Peptide according to claim 1 with Seq.Id.No: 10 of the formula:

```
    Gly Glu Pro Pro Pro Gly Arg Pro Ala Asp.
        2               5               9
```

20. Peptide according to claim 1 with Seq.Id.No: 11 of the formula:

```
        Glu Pro Pro Pro Leu Lys Pro Ala Asn.
        1               5               9
```

21. A composition comprising the peptide of claim 2.
22. A composition comprising the peptide of claim 12.
23. A composition comprising the peptide of claim 13.
24. A composition comprising the peptide of claim 14.
25. A composition comprising the peptide of claim 15.
26. A composition comprising the peptide of claim 16.

27. A composition comprising the peptide of claim 17 in admixture with a pharmaceutically acceptable solid or liquid vehicle.

28. A composition comprising the peptide of claim 18.

29. A composition comprising the peptide of claim 19 in admixture with a pharmaceutically acceptable solid or liquid vehicle.

30. A composition comprising the peptide of claim 20 in admixture with a pharmaceutically acceptable solid or liquid vehicle.

31. A composition comprising the peptide of claim 1.

32. A composition comprising the peptide of claim 3 admixture with a pharmaceutically acceptable solid or liquid vehicle.

33. A composition comprising the peptide of claim 4 in admixture with a pharmaceutically acceptable solid or liquid vehicle.

34. A composition comprising the peptide according to claim 5.

35. A composition comprising the peptide according to claim 6.

36. A composition comprising the peptide according to claim 7.

37. A composition comprising the peptide according to claim 8.

38. A composition comprising the peptide according to claim 9.

* * * * *

UNITED STATES PATENT AND TRADEMARK OFFICE
CERTIFICATE OF CORRECTION

PATENT NO.    : 6,268,346 B1
DATED         : July 31, 2001
INVENTOR(S)   : Predrag Sikiric et al.

It is certified that error appears in the above-identified patent and that said Letters Patent is hereby corrected as shown below:

Title page,
Item [76], Inventors, change:
"Predrag Sikiric, Jurisiceva 5; Marijan Petek, Visnijica 29; Sven Seiwerth, Palmoticeva 17; Zelijko Grabarevic, Lermanova12A; Ivo Rotkvic, Cvjetno naselje 1/21; Marko Duvnjak, Roza Luxemburg 4; Branko Turkovic, Bauerova 19, all of HR-41 000 Zagreb; Stiepan Mise, Ruzveltova 37, HR-58 000 Split; Ernest Suchanek, Aleja V. Popovica 125, HR-41 000 Zagreb; Boris Mildner, Kopernikova 34, HR-41 00 Zagreb; Ivan Udovicic, Ennetmoserstrasse 16, CH-6370 Stans,"
to
-- Predrag Sikiric, Zagreb; Marijan Petek, Zagreb; Sven Seiwerth, Zagreb; Zelijko Grabarevic, Zagreb; Ivo Rotkvic, Zagreb; Marko Duvnjak, Zagreb; Branko Turkovic, Zagreb; Stiepan Mise, Split; Ernest Suchanek, Zagreb; Boris Mildner, Zagreb; Ivan Udovicic, Stans, --

Item [60], Related U.S. Application Data, change:
"Provisional application No. PCT/EP93/01352, filed on May 28, 1993" to -- which is a 371 of PCT application No. PCT/EP93/01352, Filed on May 28, 1993 --.

Signed and Sealed this

Twenty-eighth Day of May, 2002

Attest:

*Attesting Officer*

JAMES E. ROGAN
*Director of the United States Patent and Trademark Office*